United States Patent

Hoffmann et al.

[11] Patent Number: 5,534,022
[45] Date of Patent: Jul. 9, 1996

[54] LEAD HAVING AN INTEGRATED DEFIBRILLATION/SENSING ELECTRODE

[75] Inventors: Drew A. Hoffmann, Los Gatos; M. Elizabeth Bush, Fremont, both of Calif.

[73] Assignee: Ventritex, Inc., Sunnyvale, Calif.

[21] Appl. No.: 343,293

[22] Filed: Nov. 22, 1994

[51] Int. Cl.⁶ .................................................. A61N 1/05
[52] U.S. Cl. ........................ 607/122; 607/123; 607/119
[58] Field of Search ................................ 607/122, 121, 607/119, 123

[56] References Cited

U.S. PATENT DOCUMENTS

| | | | |
|---|---|---|---|
| 3,942,536 | 3/1976 | Mirowski et al. | 128/419 |
| 4,161,952 | 7/1979 | Kinney et al. | 128/786 |
| 4,444,195 | 4/1984 | Gold | 607/123 |
| 4,502,492 | 3/1985 | Bornzin | 607/121 |
| 4,611,604 | 9/1986 | Botvidsson et al. | 128/784 |
| 4,760,852 | 8/1988 | Lekholm | 128/785 |
| 4,860,769 | 8/1989 | Fogarty et al. | 128/786 |
| 4,998,975 | 3/1991 | Cohen et al. | 128/419 |
| 5,007,422 | 4/1991 | Pless et al. | 28/419 |
| 5,007,436 | 4/1991 | Smits | 128/786 |
| 5,016,808 | 5/1991 | Heil, Jr. et al. | 228/176 |
| 5,052,407 | 10/1991 | Hauser et al. | 128/786 |
| 5,074,313 | 12/1991 | Dahl et al. | 128/784 |
| 5,226,260 | 7/1993 | Mar et al. | 51/319 |
| 5,318,572 | 6/1994 | Helland et al. | 607/122 |
| 5,326,448 | 7/1994 | Otten | 204/402 |
| 5,336,253 | 8/1994 | Gordon et al. | 607/122 |
| 5,342,414 | 8/1994 | Mehra | 607/127 |
| 5,370,665 | 12/1994 | Hudrlik | 607/9 |
| 5,411,544 | 5/1995 | Mar et al. | 607/122 |
| 5,431,681 | 7/1995 | Helland | 607/119 |
| 5,439,485 | 8/1995 | Mar et al. | 607/119 |

FOREIGN PATENT DOCUMENTS

| | | | |
|---|---|---|---|
| 455072A | 11/1991 | European Pat. Off. | 607/119 |
| 718324A | 12/1988 | Germany | 607/119 |

OTHER PUBLICATIONS

"Alternating Current Electrode Polarization", Schwan, *Biophysik* 3, 181–201 (1966).

U.S. patent application Ser. No. 08/126,291 entitled "Defibrillation Electrode Connection", Mar, Ventritex, Inc.

U.S. patent application Ser. No. 08/126,619 entitled "Flexible Defibrillation Electrode of Improved Construction", Mar, et al., Ventritex, Inc.

U.S. patent application Ser. No. 08/018,832 entitled "Electrical Connection for Medical Electrical Stimulation Electrodes", Bush, et al., Ventritex, Inc.

U.S. patent application Ser. No. 08/291,259 entitled "Method for Manufacturing Implantable Cardiac Defibrillation Electrodes using a Laser Beam Material Removal Process", Layman, et al., Ventritex, Inc.

Primary Examiner—William E. Kamm
Assistant Examiner—Carl H. Layno
Attorney, Agent, or Firm—Steven M. Mitchell; M. Elizabeth Bush; Mark J. Meltzer

[57] ABSTRACT

An implantable defibrillator lead having an improved integrated bipolar defibrillation electrode is disclosed. The defibrillation electrode is electrically connected to the lead conductor at the distal end, and has an increased surface area portion at the distal end, for bipolar sensing with a right ventricular pacing electrode.

32 Claims, 9 Drawing Sheets

Integrated Bipolar

Dedicated Bipolar

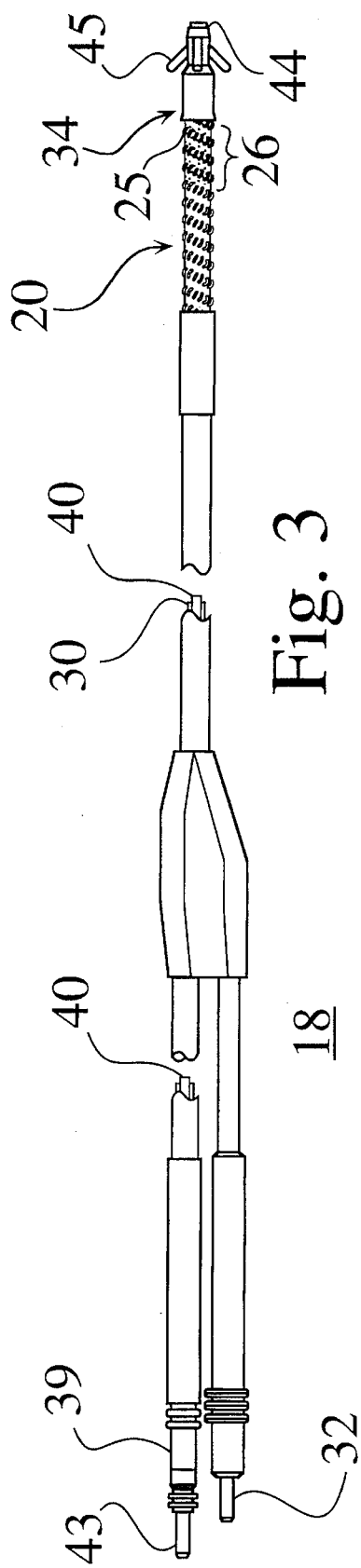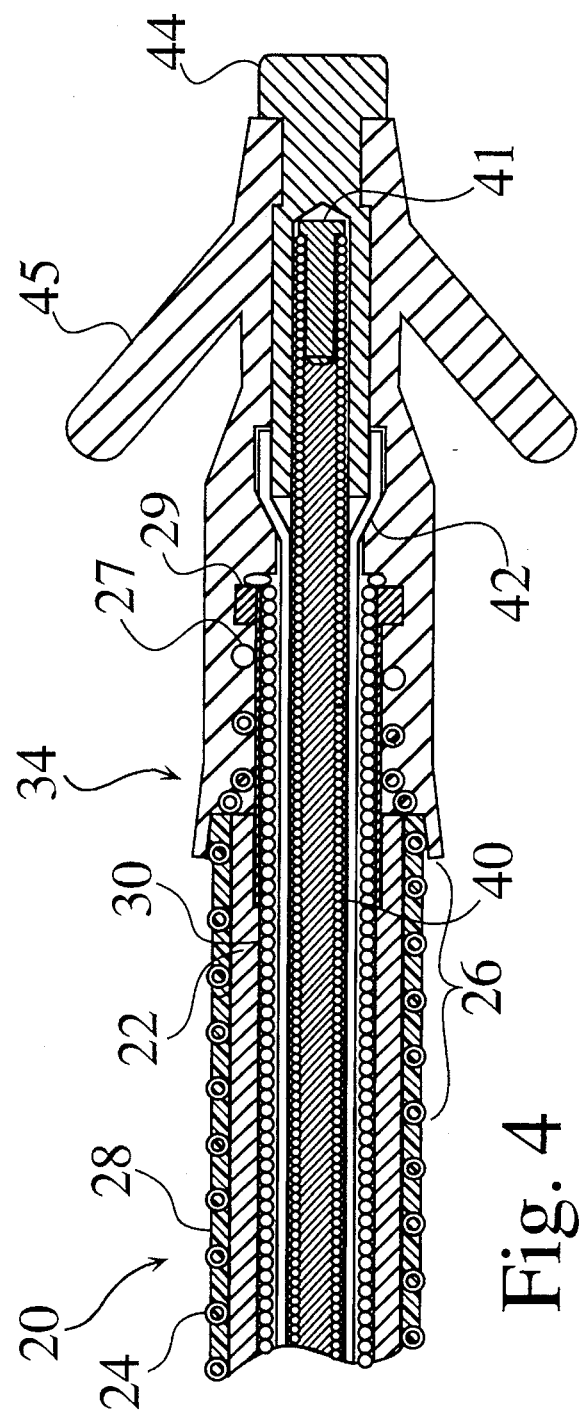

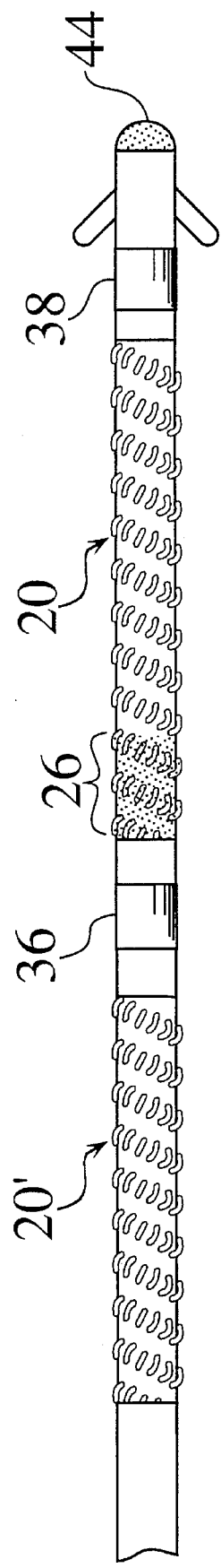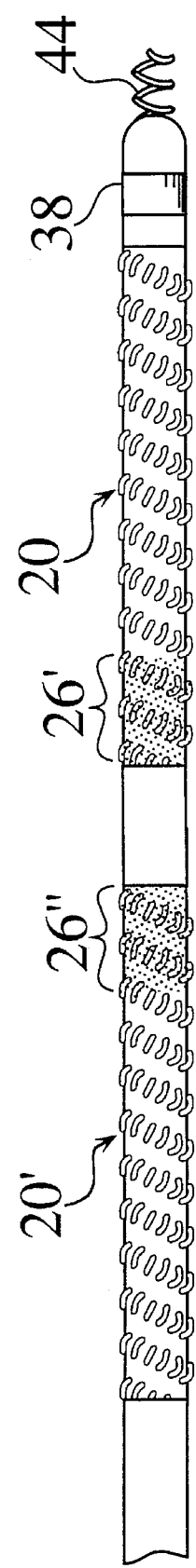
Fig. 13
Fig. 14

LEAD HAVING AN INTEGRATED DEFIBRILLATION/SENSING ELECTRODE

FIELD OF THE INVENTION

This invention relates to medical electrical stimulation electrodes in general and to implantable defibrillation electrodes in particular.

BACKGROUND OF THE INVENTION

It is well known that cardiac arrhythmias such as ventricular fibrillation may be controlled with devices such as implantable defibrillators. Many different types of defibrillation electrodes have been suggested over the years, as can be seen from the following examples. In this discussion, the term defibrillation electrode will refer to both the conductive portion of the lead that delivers current to tissues, and any supporting core material or matrix material required to hold the desired shape of the conductive portion. Also, no distinction will be made between cardioversion and defibrillation; both will be referred to as defibrillation.

U.S. Pat. No. 3,942,536 issued to Mirowski et al. discloses an intravascular bipolar catheter electrode system wherein each of two electrodes is composed of a plurality of spaced rings. As implanted, the first electrode is located within the right ventricle (RV) and the second electrode is located in the superior vena cava (SVC).

In U.S. Pat. No. 4,161,952 issued to Kinney et al., a catheter electrode has a coil of wound spring wire, with filler material beneath and between individual turns of coil such that only the outside of the wound wire is exposed to the patient's body. It is designed to reside in or about the heart.

Other types of transvenously placed leads are disclosed in U.S. Pat. No. 4,998,975 issued to Cohen et al. One lead is placed through the heart wall, and into the pericardial space, and another is placed endocardially in a conventional manner. Both leads are shown with several embodiments, with the examples of general electrode construction being to expose a section of the conductor coil, or to use ring electrodes similar to those used in conventional bipolar pacemaker leads.

Another lead system patent, U.S. Pat. No. 5,007,436 issued to Smits, describes electrodes of both J and straight configurations, for use in the RV, right atrium, great cardiac vein, or coronary sinus (CS). The fabrication methods suggested use close wound conductive coils mounted exterior to an elongated insulative sheath, or the method of Kinney et al.

Spiral shaped electrodes for endocardial, epicardial, or extrapericardial implantation are described in Heil, Jr. et al., U.S. Pat. No. 5,01 6,808, Fogarty et al., U.S. Pat. No. 4,860,769, and Hauser et al., U.S. Pat. No. 5,052,407. The electrodes of these patents use various construction techniques, including electrodeposition or vapor deposition onto a plastic tube, helically wound wire (round or ribbon, unifilar or multifilar, single or double helix) or conductive rings on a flexible insulating portion, and conductive screen wrapped around a tubular body.

In U.S. Pat. No. 5,439,485 to Mar et al., assigned to the assignee of the present application, small diameter helically wound coils are wound onto a flexible core. These "electrode coils" are partially encapsulated by a flexible matrix which holds them in their wrapped position about the core.

Commercially available transvenous defibrillation / pacing leads provide sensing through either "integrated" or "dedicated" (also known as "true") bipolar electrode configurations. FIGS. 1 and 2, respectively, show Prior Art integrated and dedicated leads. In the integrated configuration, the pacing tip electrode 44 and defibrillation electrode 20 serve as the bipolar pair for sensing. In the dedicated configuration, a sensing ring 38 near the pacing electrode 44 and electrically isolated from the defibrillation electrode 20 forms a bipolar pair with the pacing electrode 44. In the integrated configuration, the defibrillation electrode 20, serving as one electrode of the bipolar pair, is relatively large.

If the bipolar signal is considered as an algebraic sum of unipolar signals measured at each pole of the bipolar pair of electrodes with reference to a remote electrode, then the difference between the integrated and dedicated configurations described above can be considered. Since the pacing tip is in intimate contact with the electrically active endocardial tissue and is small, the signal transmitted by this electrode is of relatively large amplitude and small pulse duration. The depolarization-repolarization wavefront will be sensed as it passes the electrode over a short distance. The unipolar signal sensed by the defibrillation electrode with respect to a remote electrode is smaller in amplitude and broader in pulsewidth. The lower amplitude is to be expected due to the remote location of the electrode in the blood pool, possibly covered with a layer of electrically inactive cells. The broader pulsewidth arises from the larger size of this electrode. The depolarization-repolarization wavefront may be sensed by the defibrillation electrode for a longer period of time as it spreads through the septum and right ventricle. A unipolar signal from a lead having a dedicated sensing ring with reference to a remote electrode represents a case intermediate unipolar sensing from the tip electrode and unipolar sensing from the defibrillation electrode, in that the ring is still fairly remote from active tissue like the defibrillation electrode but is smaller and closer to the pacing tip. As a result, the sensing ring signal amplitude is smaller than that sensed by the pacing electrode, but the sensed pulsewidth is narrower than for the defibrillation electrode.

To compare a dedicated bipolar signal to an integrated bipolar signal, the sum of the unipolar tip electrode signal and the unipolar ring electrode signal can be compared with the sum of the unipolar tip electrode signal and the unipolar defibrillation electrode signal. Thus, the dedicated bipolar configuration may be expected to produce a sharper bipolar sensing signal than the integrated bipolar configuration.

A problem with the use of the dedicated sensing ring is that it forces the defibrillation electrode to be located further from the cardiac tissue, and to be made shorter, assuming the length is constrained by the length of the ventricular chamber (apex to tricuspid valve); both the change in location and in length raise the defibrillation threshold. The dedicated sensing ring also requires not only an additional electrode but also an additional conductor, which may add cost, complexity, and / or lead size, or necessitate the use of new conductor technology. It also adds stiffness to the end of the lead, increasing the potential for perforations and exit block. However, the advantage of localized sensing makes the dedicated sensing electrode desirable.

In pacing electrode technology, the geometric dimensions of the electrode are minimized to increase the current density in adjacent tissue thereby lowering the stimulation threshold. However, sensing impedance is governed by the capacitive double layer at the surface of the electrode. From this standpoint, the larger the surface area, the lower will be the sensing impedance. Typically, microscopic electrode surface area is increased, for example by providing a porous surface structure, to reduce the sensing impedance. This surface structure is often used to advantage in pacing tip electrodes to encourage viable cell ingrowth, thereby increasing sensing signal amplitudes and decreasing stimulation thresholds.

SUMMARY OF THE INVENTION

The present invention provides a lead with an improved electrode design for use with an implantable defibrillator system. In the present invention, the principle of using surface texture to minimize sensing impedance is used to incorporate the function of localized sensing into an integrated bipolar electrode system. In this way the advantages of the localized, dedicated sensing electrode may be achieved without the need for a separate electrode and additional conductor.

In the preferred embodiment, the most distal 1 to 5 mm of the defibrillation electrode is covered with a porous coating such as platinum black, ruthenium oxide, activated carbon, titanium nitride, iridium oxide, or sintered platinum. This portion of the electrode will have a much lower interfacial impedance than non-coated areas. As a result, although the entire electrode is in electrical contact, the signal passing the coated, distal end will have the greatest sensed amplitude. In effect, in the sensing function, only the treated portion of the electrode will be active. Considering the electrode as a transmission line, the interfacial capacitors would be very large in the treated portion of the electrode and much smaller in the untreated areas. Platinum black can produce as much as a 10,000-fold increase in surface area which would clearly separate the impedance of treated and untreated areas. During defibrillation, the entire electrode will be operative in delivering current to the tissue. Since the impedance at high current density is less dependent on interfacial polarization, defibrillation current distribution will not be significantly altered.

In one embodiment, a transvenous electrode is constructed from six tiny platinum iridium space wound coils, space wound onto a silicone rubber tube, molded over with silicone rubber, then partially exposed. The distal end of the electrode is immersed in an appropriate electrolytic solution and platinum black is electrodeposited onto this area. Alternatively, the coating may be applied by a sputter or reactive sputtering process, masking the portions of the electrode that are to be used only for defibrillation and not for sensing. A thin surface coating may cover both rubber and metal to further advantage.

This electrode exhibits a high degree of flexibility and therefore can be positioned quickly and easily within the right ventricle, for example. The use of small coiled coils may provide an electrode having a resistance greater than about one ohm. While prior art systems attempt to minimize electrode resistance, this feature is used to advantage with the present invention wherein current flow from the electrode may be controlled or modified by changing the location where the lead conductor is electrically connected to the electrode. By connecting the conductor to the distal portion of the electrode, a larger portion of the current for both sensing and defibrillation will flow through the distal portion.

In another embodiment using a segmented defibrillation electrode, the most distal segment may be fabricated from a material suitable for sensing, as described above.

This invention also presents the advantage of reducing interfacial current density at the distal end during defibrillation which will raise the threshold at which arcing occurs in distally connected electrodes.

The present invention may also be used for other site specific sensing. For example, in a lead with bipolar ventricular and atrial sensing, the most proximal end of the ventricular defibrillation electrode may be treated and serve as one electrode of the atrial bipolar electrode pair. In that case, a dedicated ventricular sensing ring may be required.

In another embodiment, with a defibrillation electrode that is affixed to the RV apex, RV freewall or the septum, as for example by the method of Fain et al. in patent application Ser. No. 08/170,133, which is assigned to the assignee of the present application and is incorporated herein by reference, the electrode surface area nearest the fixation site is increased to provide both localized sensing and localized tissue ingrowth, resulting in an increase in sensing electrode signal amplitude along with the reduction in pulsewidth already discussed, and allows sensing of the bundle of His.

In an alternative embodiment, this electrode construction may be used on a lead designed for epicardial placement.

It is thus an object of the present invention to provide a lead with an improved electrode for an implantable defibrillator.

It is an additional object of the invention to provide a lead with an integrated bipolar electrode system that provides a higher amplitude, lower pulsewidth signal than existing integrated bipolar electrode systems.

It is another object of the invention to provide a lead with an electrode that is more easily manufactured.

It is another object of the invention to provide a method of electrode construction that can be used to enhance the performance of the electrode configurations of the prior art.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which:

FIG. 3 illustrates the defibrillation lead of novel construction of the present invention;

FIG. 4 is a detail cross sectional view of the distal portion of the o lead of FIG. 3;

FIG. 13 shows a lead with bipolar ventricular and atrial sensing, wherein the most proximal end of the ventricular defibrillation electrode is treated and serves as one electrode of the atrial bipolar electrode pair; and FIG. 14 shows a lead in which the atrial signal is sensed using two effective sensing electrodes, one on the distal end of the proximal defibrillation electrode and one on the proximal end of the distal defibrillation electrode.

DETAILED DESCRIPTION OF THE INVENTION

Figure 1:
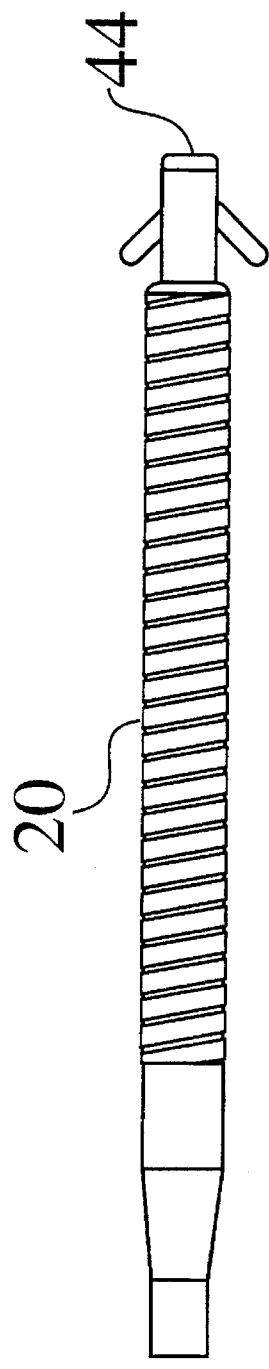
FIG. 1 shows an electrode configuration of the prior art having integrated sensing.
Figure 2:
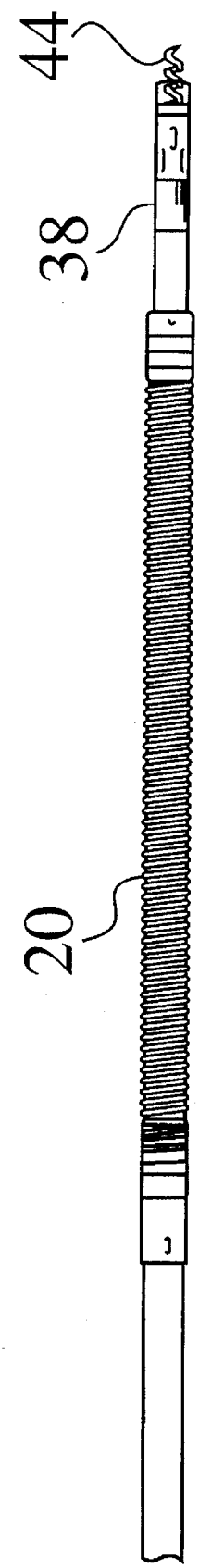
FIG. 2 shows an electrode configuration of the prior art having dedicated sensing.

FIG. 3 shows a lead 18 with a pacing electrode 44 which is used alternately for pacing and sensing, and a defibrillation electrode 20 which is used alternately for defibrillation and for sensing. Pacing electrode 44 may be of any of the numerous constructions known in the art. A fixation mechanism 45 is shown as tines, but may be any known in the art, including a screw used for both pacing and fixation. Pacing electrode 44 is electrically connected to a pacing conductor coil 40, which is in turn connected to a pacing connector 43. Defibrillation electrode 20 is electrically connected at connection 34 to a defibrillation conductor coil 30, which is electrically connected to both a defibrillation connector 32 and a sensing connector ring 39. The most distal 1 to 5 mm of the defibrillation electrode 20 is covered with a porous coating such as platinum black, ruthenium oxide, activated carbon, titanium nitride, iridium oxide, sintered platinum, or otherwise has an increased surface area portion 26, such as by etching or electrolytically roughening. Alternatively, this portion may be made from a material having very low polarization, such as Ag/AgCl. This portion 26 of the electrode will have a much lower interfacial impedance than non-coated areas. As a result, although the entire electrode is in electrical contact with cardiac tissue, the signal passing the coated, distal end will have the greatest sensed amplitude. In effect, in the sensing function, only the treated portion 26 of the defibrillation electrode 20 will be active. For example, platinum black can produce as much as a 10,000-fold increase in surface area which would clearly separate the impedance of treated and untreated areas. The treated portion of the electrode would have a much larger interfacial capacitance and lower resistance than the untreated areas. During defibrillation, the entire conductive portion of defibrillation electrode 20 will be operative in delivering current to the cardiac tissue because at high current, impedance is less affected by interfacial characteristics. In the preferred embodiment, treated portion 26 acts as an effective sensing electrode which is paired with pacing electrode 44 for bipolar sensing. The spacing between the treated portion 26 at the distal end of defibrillation electrode 20 and pacing electrode 44 is preferably between 3 and 20 millimeters.

FIG. 4 shows a detail cross sectional view of the distal portion of lead 18 of FIG. 3. Defibrillation electrode 20 is shown to be constructed of a plurality of electrode coils 24 helically wound around a flexible tubular supporting core 22, which may be either electrically conductive or insulative, and may be extruded or molded. This structure has elastomeric matrix material 28, which may be either electrically conductive or insulative, partially encapsulating the electrode coils. The elastomeric matrix material 28 may alternatively be conductive in the portion of the electrode desired to be used for sensing, and may be insulative in the regions intended to be used only for defibrillation. The surface texture of a conductive matrix may be altered to make it more porous in the sensing region; the surface texture of a partially conductive matrix may be altered to make it more porous in the sensing region, or over the entire surface, since texturizing the nonconductive portion would have no effect on the impedance, and therefore on sensing. In that case, the "effective sensing electrode" comprises the portion of exposed electrode coil with increased surface area as well as the surface of the matrix material in that region. In the case where the matrix material 28 is nonconductive, the matrix material may be coated or impregnated with a conductive material to increase conductive surface area in the sensing region. In that case, the "effective sensing electrode" comprises the portion of exposed electrode coil with increased surface area as well as the coated or impregnated surface of the matrix material.

The many electrode coils 24 increase conductivity and redundancy. One method of achieving this structure is to completely encapsulate the wrapped electrode coils, then abrade away the surface to partially expose the coils using the method of Mar et al., U.S. Pat. No. 5,226,260, which is assigned to the assignee of the present application and which is incorporated herein by reference. Alternatively, the coils may be partially exposed by ablating the elastomeric material 28 using the laser material removal process of the copending U.S. patent application Ser. No. 08/291,259 filed Aug. 16, 1994 by Layman et al. which is assigned to the assignee of the present application and which is incorporated herein by reference. The level of material removal is controllable; the more metal exposed, the greater the electrode surface area for defibrillation, but the less material for providing mechanical stability. The lead body diameter is generally about 2.5 to 4.5 mm.

Defibrillation conductor coil 30 is welded to the face of a sleeve 29, as described in U.S. patent application Ser. No. 08/018,832, filed Feb. 18, 1993 by Bush et al., for an "Electrical Connection for Medical Electrical Stimulation Electrodes" which is assigned to the assignee of the present application and which is incorporated herein by reference. Alternatively, this connection may be a laser weld, a crimp, or the like. The conductor coil 30 is in turn electrically connected to a defibrillation connector 32 for coupling with a pulse generator such as the type described in U.S. Pat. No. 5,007,422 to Pless et al., which is assigned to the assignee of the present application. Pacing conductor coil 40 extends through the lumen of tubular core 22 and is electrically insulated from conductor coil 30 by an insulator 42. Pacing conductor coil 40 is shown connected by a crimp connection to pacing electrode 44 and a crimp pin 41; this connection may alternatively be a weld.

Figure 5:
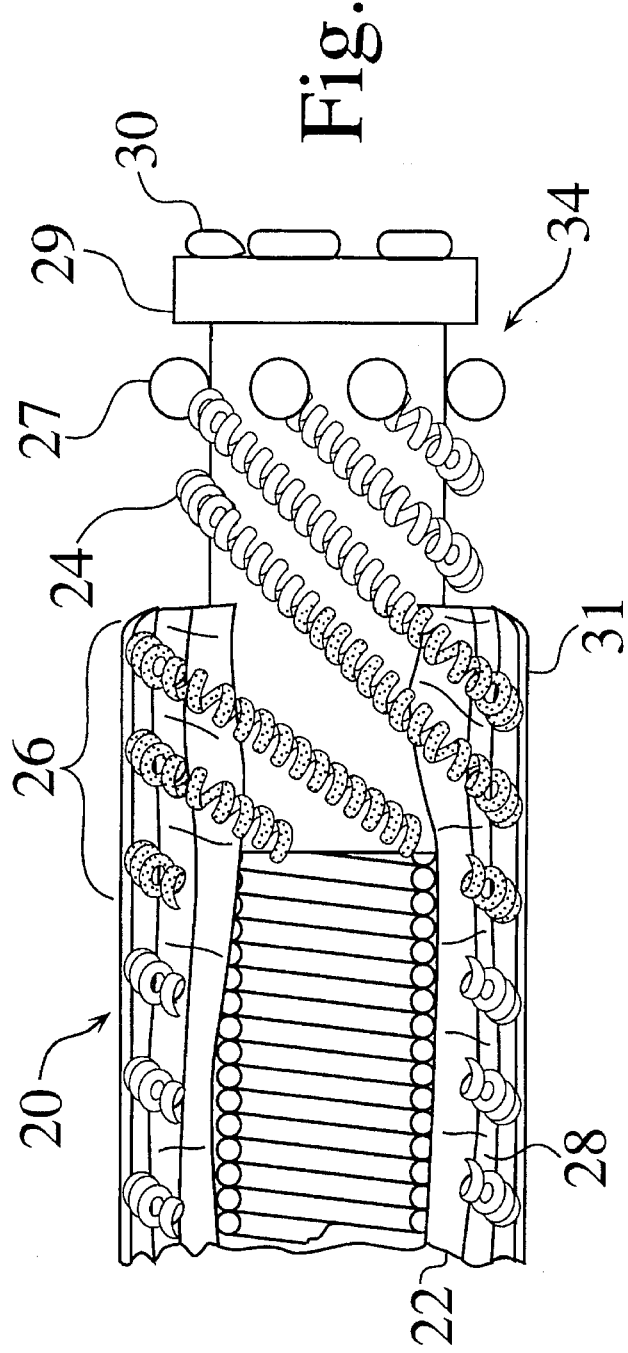
FIG. 5 is a detail view, partly in cross section, of the electrode to conductor connection of the electrode of FIG. 4.

FIG. 5 is a detail view, partly in cross section, of the electrode to conductor connection of the electrode of FIG. 4, and shows that each electrode coil 24 in the preferred embodiment is made from a helically wound metal wire, which may be round or flat in cross section. This wire must be very strong, fatigue resistant, conductive, corrosion resistant, and biocompatible. Platinum iridium is one example of such a material. Electrode coil 24 is shown without an inner core; however, a thin wire or plastic filament could be located within coil 24 to provide either increased electrical conductivity, mechanical redundancy, or both. The filament could be metal or nylon, for example. In order for the lead to be sufficiently thin to be transvenously implantable, electrode coils 24 should be between about 0.2 and 0.4 mm, and wire should be about 0.05 to 0.10 mm in diameter. Close winding of wire into electrode coils 24 provides more exposed metal for charge transfer to tissue. However, space winding decreases the lengths of wire in the coils, decreasing end to end electrode resistance. Additionally, space winding provides more surface for matrix material to mechanically stabilize coils and allows for a substantial volume of matrix material that can flex with the heart and body motion instead of pulling away from the coils. Therefore, a certain amount of space is preferred, typically one-half to one wire diameter space between wires. Similarly, electrode coils 24 can be close or space wound onto core 22. The same general principles apply. The distal end of each electrode coil 24 is melted into a ball 27, which provides more volume of material to form a strong and reliable crimp or weld, and is then welded to sleeve 29, forming electrical connection 34 to the defibrillation conductor coil 30. This connection is also described in U.S. patent application Ser. No. 08/126,291, filed 1993 by Mar, for a "Defibrillation Electrode Connection" which is assigned to the assignee of the present application and is incorporated herein by reference. This melted ball structure works particularly well when made of a noble material such as a platinum iridium alloy. A hydrogen torch, also called a "water welder", is one suitable means for melting the coil to form the ball. This device dissociates water into hydrogen and oxygen, then burns the hydrogen to form water again. This process burns cleanly, without incorporating byproducts into the melting coil, which is important for maintaining biocompatibility and material consistency for any subsequent welding.

Because the electrode coil wire is longer and thinner than the electrode elements of the prior art, the electrode of the present invention can be made with a certain amount of resistance along its length, say, 3 to 15 ohms. This property of the electrode can be used to direct defibrillation energy to selected regions of the heart by careful choice of connection locations of electrode to conductor. For example, if the defibrillation electrode 20 were placed with its distal end in the apex of the RV, current would be steered to the RV apex since that is where the conductor attaches to the electrode at connection 34. Likewise, sensed signals would come mainly from the RV apex. Increasing the surface area of electrode 20 in this region, forming the effective sensing electrode at treated portion 26, will further enhance charge transfer, thereby increasing current flow through it.

One method of increasing or enhancing the surface area of defibrillation electrode 20 to form effective sensing electrode 26 of the lead having a coiled coil electrode of the type described above, is to mask the regions that are not desired to be coated, then immerse the entire electrode 20, or just the portion to be coated, into an electrolytic solution and electrodeposit platinum black onto the exposed portion of metal electrode coil 24. This process is described in an article by H. P. Schwan, entitled Alternating Current Electrode Polarization, in *Biophysik* 3, 181–201 (1966), which states, "The electrode is inserted into a solution of 0.025N hydrochloric acid containing 0.3% platinum chloride and a trace of lead acetate (0.025%). A DC-current is then passed through the solution, utilizing platinum as a second electrode in order to avoid poisoning of the solution. Platinum is deposited at the electrode to be covered if the latter is arranged as cathode. The current density recommended . . . is 30 mA per $cm^2$ electrode surface." By this process, the platinum will coat the exposed portion of metal electrode coils 24, but not the elastomeric matrix 28. Alternatively, a porous coating may be sputtered or reactively sputtered onto the unmasked portion of the electrode. A soluble protective coating 31, such as mannitol, may be provided over the platinum black or other conductive coating to keep it from rubbing off during implant.

Figure 6:
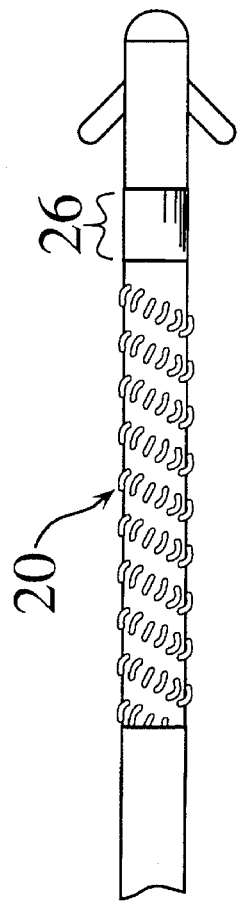
FIG. 6 illustrates an alternative embodiment having a solid ring portion in the sensing region of the defibrillation electrode.

FIG. 6 illustrates an alternative embodiment wherein defibrillation electrode 20 has a solid conductive ring forming the increased surface area portion 26 for sensing. The ring may be smooth or porous. A smooth ring would provide an increase in macroscopic surface area in that region as compared with the surface area that would be provided using the structure of the remainder of the electrode, such as the coil of Kinney et al. or coiled coil as described above. A porous ring would provide an increase in both macroscopic and microscopic surface area as compared with the surface area provided using the structure of the remainder of the electrode.

Figure 7:
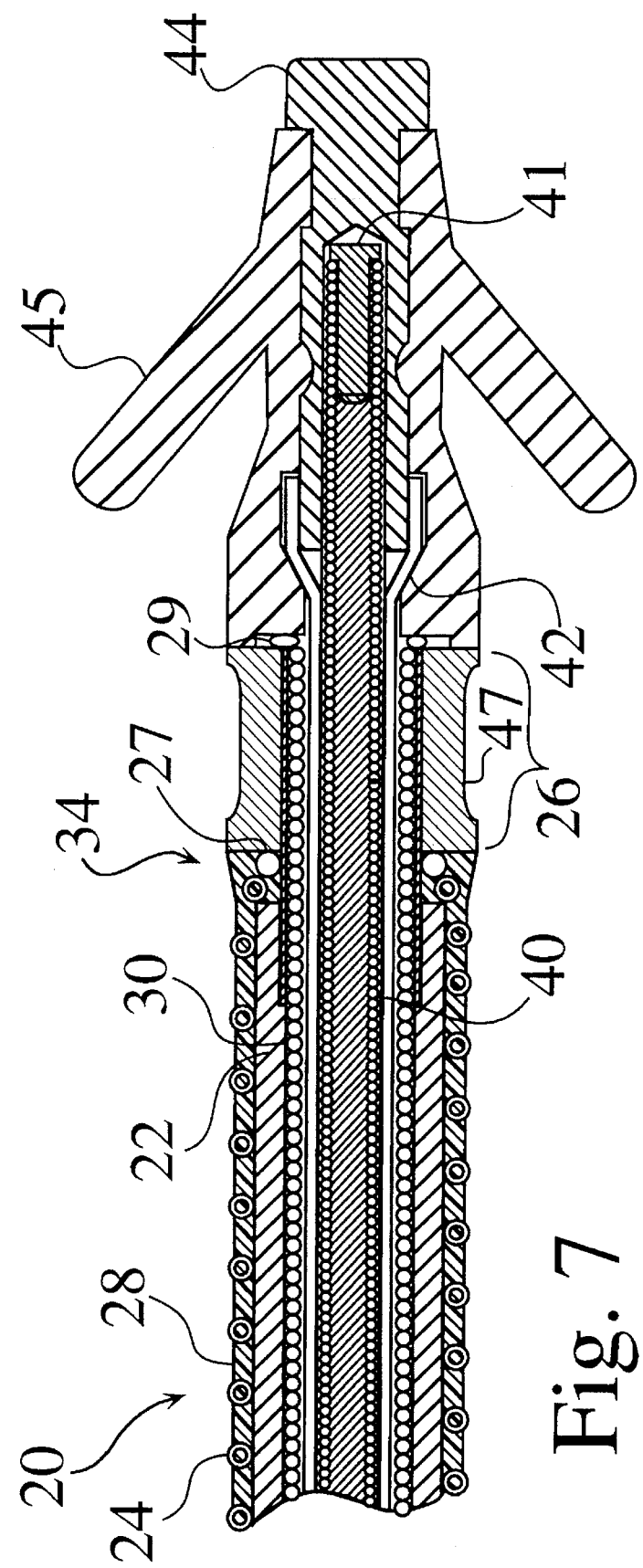
FIG. 7 is a detail cross sectional view of the distal portion of an alternative embodiment of the lead of FIG. 4.
Figure 8:
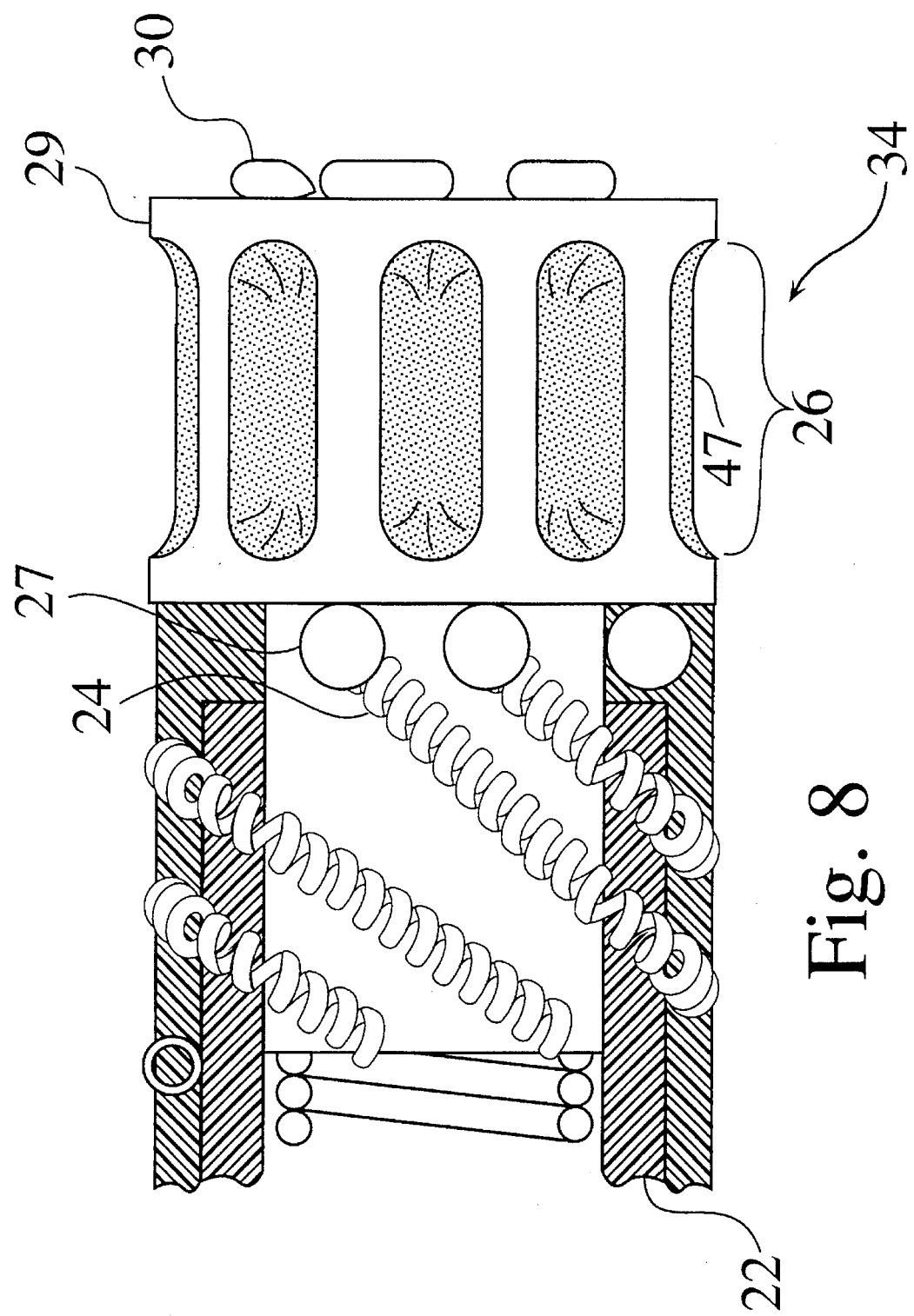
FIG. 8 is a detail view, partly in cross section, of the electrode of FIG. 7.

FIG. 7 is a detail cross sectional view of the distal portion of an alternative embodiment of the lead of FIG. 4, and FIG. 8 is a detail view, partly in cross section, of the electrode of FIG. 7. In this embodiment, the sleeve 29 is of approximately the same diameter as the overall diameter of the exposed coiled electrode coils 24. Sleeve 29 is at least partially exposed to the body, forming a portion 26 that has greater surface area compared to the coiled coil portion of the electrode, and is preferably made of a platinum alloy or other corrosion resistant, biocompatible material. Sleeve 29 preferably has recesses 47 that have an increased surface area compared to the base material, further increasing the surface area of portion 26. This increased surface area may be manufactured by treating the surface of the recesses 47 with platinum black. A benefit of this configuration is that the platinum black treated area would be protected from the implanting surgeon's fingers, since if the surgeon were to touch the sleeve 29, he would be gripping only the nonrecessed regions. Likewise, the recessed, treated area would be protected from rubbing off on the patient's tissues during implant. Alternatively, the recessed area may be coated with titanium nitride or the like, or may be roughened to produce an increased surface area. Sleeve 29 may be used as a weld sleeve for conductor 30, as described for FIGS. 4 and 5; alternatively, conductor 30 may be electrically attached to defibrillation electrode 20 by other means known in the art.

Figure 9:
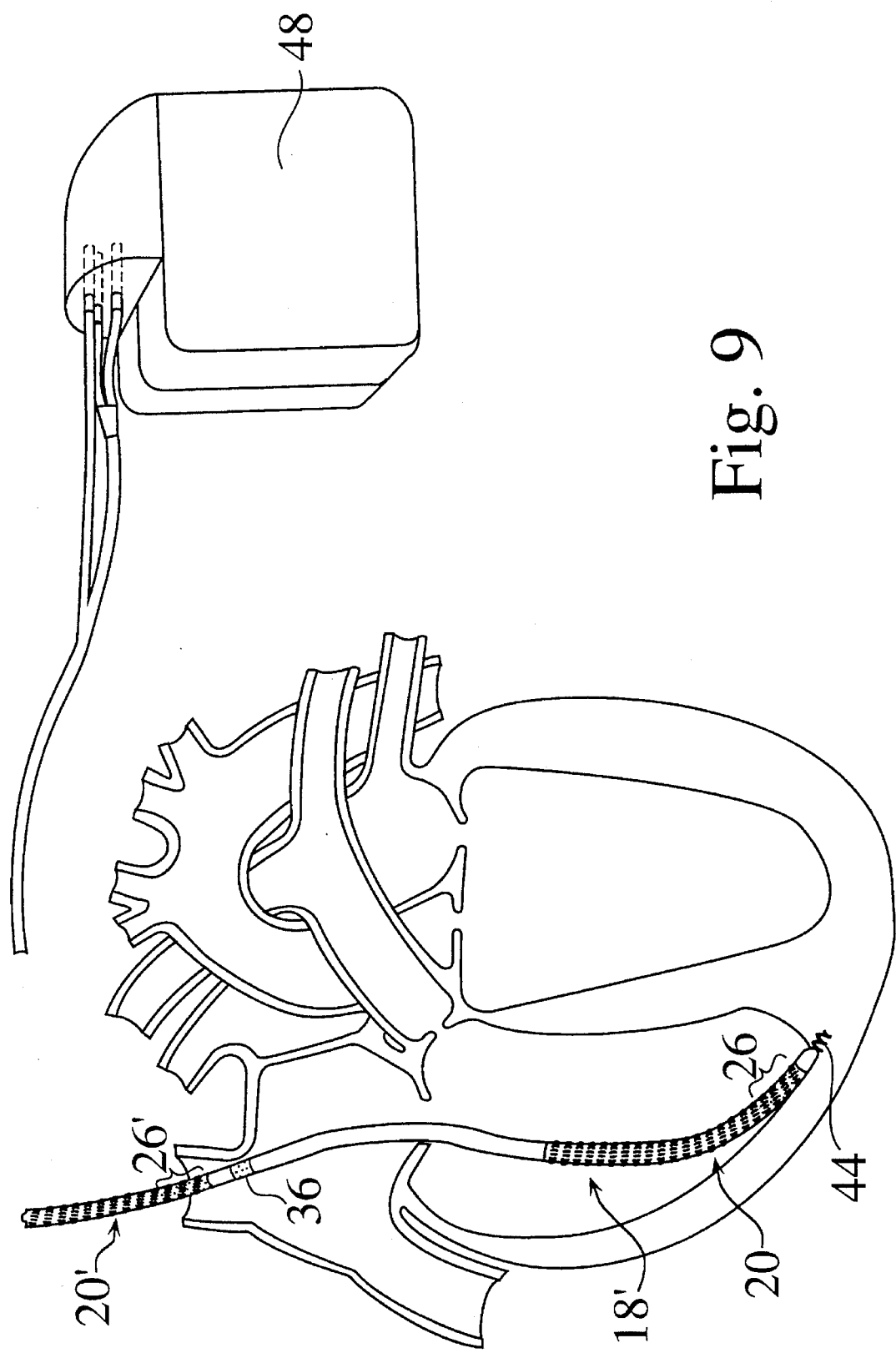
FIG. 9 shows a lead implanted in the heart that includes two defibrillation electrodes and a pacing electrode.

FIG. 9 shows a lead 18' with two defibrillation electrodes, 20 and 20', which may have opposite polarity, and a pacing electrode 44 as it is positioned within a patient's heart. Defibrillation electrode 20 acts alternately as a defibrillation electrode and as a sensing electrode. The lead is shown as situated in the heart, with pacing electrode 44 and distal defibrillation electrode 20 in the right ventricle, and proximal defibrillation electrode 20' located in the superior vena cava. If atrial sensing is desired, an atrial sensing ring 36 may be provided to be paired with electrode 20' for bipolar sensing. In that case, the distal end of proximal electrode 20' would have an increased surface area portion 26' to form an effective sensing electrode. A defibrillation pule generator 48 is connected to the proximal end of defibrillation lead 18'.

Figure 10:
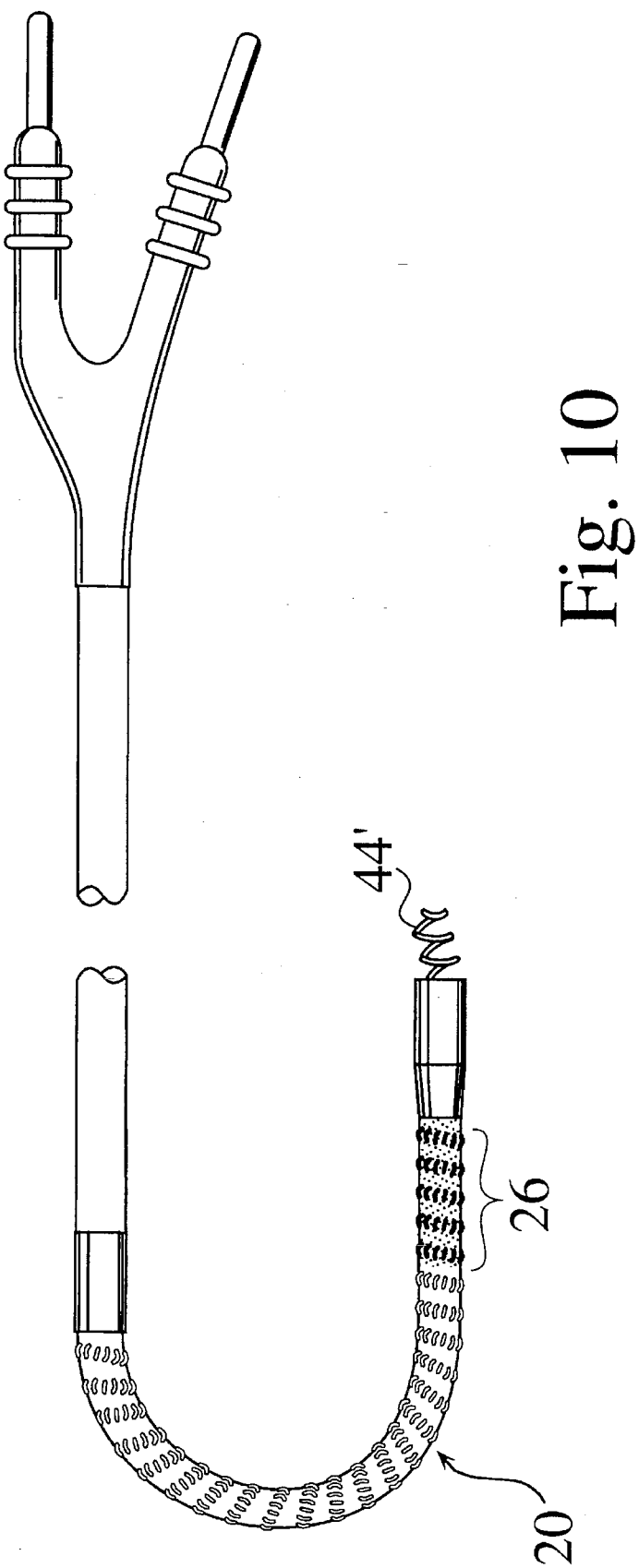
FIG. 10 is a J electrode for placement in the right atrium.

FIG. 10 is a J electrode having a pacing electrode 44' for placement in the right atrium. A portion of electrode 20 has an increased surface area to form an effective sensing electrode 26 to be used with pacing electrode 44' to form an bipolar pair.

Figure 11:
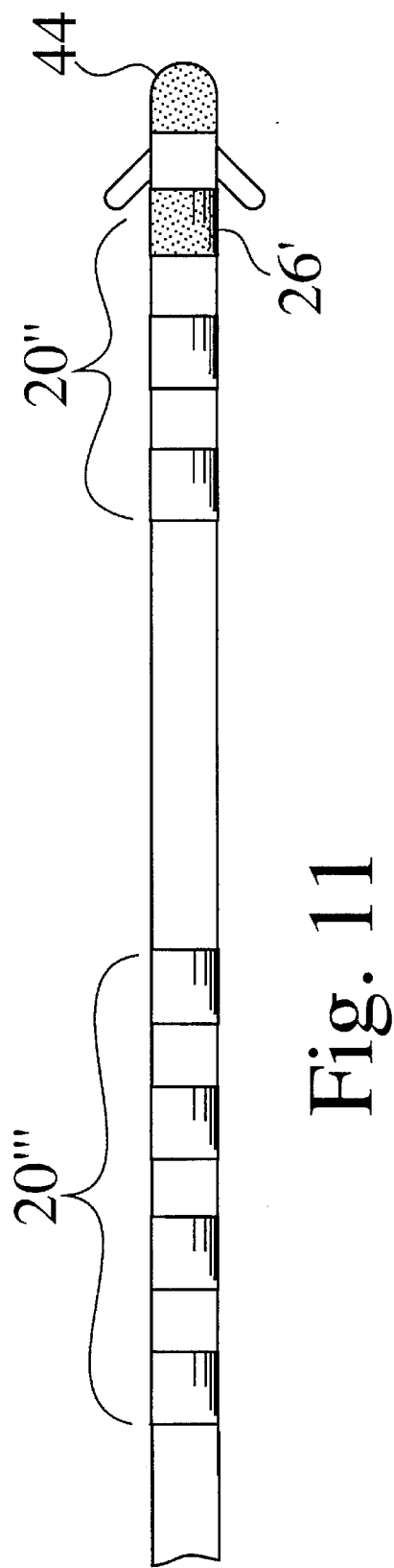
FIG. 11 illustrates an alternative embodiment having ring electrodes.

FIG. 11 illustrates an alternative embodiment having two segmented electrodes 20" and 20''', and a pacing electrode 44. Using a segmented defibrillation electrode, the most distal segment 26' is fabricated from a material suitable for sensing, such as Pt black, ruthenium oxide, activated carbon, titanium nitride, iridium oxide, or sintered platinum as described above.

Figure 12:
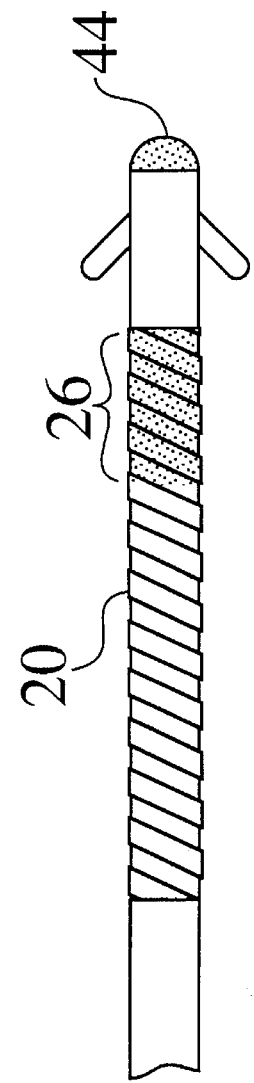
FIG. 12 illustrates a further embodiment having wound ribbon.

FIG. 12 illustrates a further embodiment having a defibrillation coil of wound ribbon. The most distal portion has an increased surface area 26 to form an effective sensing electrode.

FIG. 13 shows a lead with bipolar ventricular and atrial sensing, wherein the most proximal end of the ventricular defibrillation electrode is treated, 26', and serves as one effective sensing electrode, and atrial sensing ring 36 as the other electrode, of the atrial bipolar electrode pair. For atrial sensing purposes, the distal electrode 20 is preferably connected to its conductor at its proximal end. A dedicated ventricular sensing ring 38 is paired with pacing electrode 44 for bipolar ventricular sensing.

FIG. 14 shows a lead with bipolar ventricular and atrial sensing, wherein the effective sensing electrodes, increased surface area portions 26' and 26", are paired for atrial sensing. The distal electrode 20 is preferably connected to the internal conductor at its proximal end to provide the least resistance to sensing for the effective sensing electrode, portion 26. Likewise, proximal electrode 20' is preferably connected at its distal end. Dedicated sensing ring 38 is paired with pacing electrode 44 for bipolar ventricular sensing.

The above has been offered for illustrative purposes only and is not intended to limit the scope of the invention of this application, which is as defined in the claims below.

That which is claimed is:

1. A body implantable lead comprising:
   an elongated insulated lead body;
   a first defibrillation electrode having first and second ends;
   a connector at a proximal end of said lead body for connection of said lead with a defibrillator;
   a conductor mounted in said lead body and attached to said defibrillation electrode, forming a defibrillation electrode attachment, and to said connector; and
   said defibrillation electrode having an increased surface area portion thereon to form an effective sensing electrode region, wherein said increased surface area portion covers less than the entirety of said first defibrillation electrode.

2. The lead of claim 1, wherein said portion of said defibrillation electrode having an increased surface area portion is located at said first end of said defibrillation electrode.

3. The lead of claim 1, wherein said defibrillation electrode attachment is located at one of said ends of said defibrillation electrode and wherein said portion of said defibrillation electrode having an increased surface area is located at said first end.

4. The lead of claim 1, wherein said increased surface area portion extends from said first end to approximately 1 to 5 millimeters from said first end.

5. The lead of claim 1, wherein said increased surface area portion comprises a porous coating.

6. The lead of claim 5, wherein said porous coating is chosen from the group consisting of platinum black, ruthenium oxide, activated carbon, titanium nitride, iridium oxide, and sintered platinum.

7. The lead of claim 1, and further including a soluble coating on said increased surface area portion.

8. The lead of claim 1, wherein said increased surface area portion comprises an electrically conductive ring.

9. The lead of claim 8, wherein said ring includes at least one recess having a porous surface.

10. The lead of claim 1, wherein said defibrillation electrode comprises a plurality of longitudinally spaced elements, and wherein one of said elements comprises said increased surface area portion.

11. The lead of claim 10 wherein each of said elements comprises a ring.

12. The lead of claim 1, and further including:
    a pacing electrode;
    a pacing conductor coupled with said pacing electrode; and
    a pacing connector coupled with said pacing conductor, wherein said pacing electrode is paired with said defibrillation electrode for bipolar sensing.

13. The lead of claim 12, wherein said defibrillation electrode and said pacing electrode are spaced from each other by between 3 and 20 mm.

14. The lead of claim 2 wherein said first end is the distal end of said defibrillation electrode.

15. The lead of claim 2, wherein said first end is the proximal end of said defibrillation electrode.

16. The lead of claim 15, and further including:
    an atrial ring electrode mounted on said lead body;
    an atrial ring electrode conductor coupled to said atrial ring electrode; and
    an atrial ring electrode connector coupled to said atrial ring electrode conductor, wherein said atrial ring electrode is paired with said increased surface area portion of said defibrillation electrode for bipolar atrial sensing.

17. The lead of claim 15, and further including a second defibrillation electrode located proximal to said defibrillation electrode, said second defibrillation electrode having an increased surface area on a distal portion thereof to form a second effective sensing electrode region, wherein said effective sensing electrode region of said first defibrillation electrode and said second effective sensing electrode region of said second defibrillation electrode are paired for atrial sensing.

18. The lead of claim 17, and further including a ventricular sensing electrode and a ventricular pacing electrode located on a distal end of said lead body, paired for ventricular sensing.

19. The lead of claim 1, wherein said defibrillation electrode further comprises:
    a flexible supporting core having a lumen therethrough;
    at least one electrode coil helically wound about said core, said at least one electrode coil comprising at least one helically wound metal wire and being connected at one end to said conductor;
    a matrix of flexible material partially encapsulating said electrode coil and holding said electrode coil in said helically wound position around said core; and
    wherein said increased surface area portion comprises a covering of porous material.

20. The lead of claim 19 in which said matrix is conductive.

21. The lead of claim 19 in which a portion of said matrix located on said first end having an increased surface area portion has a surface texture that is more porous than the surface texture of the remainder of said matrix.

22. The lead of claim 19 in which a portion of said matrix is electrically conductive in a region located on said first end having an increased surface area portion, and the remainder of said matrix is electrically insulating.

23. The lead of claim 19 in which said conductor is electrically connected to said electrode coil at a distal end of said electrode coil.

24. A method of manufacturing a body implantable electrode for use with a pulse generator, comprising the steps of:
    providing a core;

winding at least one wire about said core;

applying an elastomeric matrix material onto said core and said wire; and applying a porous coating to one end of said electrode to cover less than the entire surface of said electrode.

25. The method of claim 24 wherein said wire is coiled prior to winding about said core.

26. The method of claim 24, wherein said step of applying a porous coating to one end of said electrode further comprises the step of immersing only said end of said electrode in an electrolytic solution and electrodepositing platinum black onto said end.

27. The method of claim 24, wherein said step of applying a porous coating to one end of said electrode further comprises the step of masking a portion of said electrode not to be coated, then sputtering said porous coating onto said end of said electrode.

28. The method of claim 24, wherein said step of applying a porous coating to one end of said electrode further comprises the step of masking a portion of said electrode not to be coated, then reaction sputtering said porous coating onto said end of said electrode.

29. A body implantable lead comprising:

an elongated insulated lead body;

a defibrillation electrode positioned on and extending along the length of said lead body and having a resistivity along its length of greater than one ohm;

a conductor mounted in said lead body and connected at one end to said defibrillation electrode at a location along the length of said electrode and at the other end to a connector for connection to an implantable pulse generator; and a porous surface coating on a portion of said defibrillation electrode at said location of the connection between said conductor and said electrode, wherein said porous surface coating covers less than the entirety of said defibrillation electrode.

30. A body implantable lead including at least one defibrillation electrode having a coated surface portion and an uncoated surface portion, wherein both said coated and uncoated surface portions are electrically coupled to a defibrillator pulse generator to make said coated and uncoated surface portions electrically active during defibrillation, and wherein said uncoated surface portion has a higher effective interfacial impedance than said coated surface portion whereby said uncoated surface portion is substantially inactive during sensing.

31. A body implantable lead including at least one defibrillation electrode having a low interfacial impedance portion and a high interfacial impedance portion electrically coupled to a defibrillator pulse generator to make both said portions active during defibrillation and said high interfacial impedance portion substantially inactive during sensing.

32. The lead of claim 31 wherein said low interfacial impedance portion comprises Ag/AgCl.

* * * * *